United States Patent
Liess et al.

(10) Patent No.: US 12,133,733 B2
(45) Date of Patent: Nov. 5, 2024

(54) PRODUCTION METHOD FOR NOBLE METAL ELECTRODES

(71) Applicant: Heraeus Deutschland GmbH & Co. KG, Hanau (DE)

(72) Inventors: Andreas Liess, Hanau (DE); Oliver Keitel, Hanau (DE); Robert Sievi, Hanau (DE)

(73) Assignee: Heraeus Deutschland GmbH & Co. KG, Hanau (DE)

( * ) Notice: Subject to any disclaimer, the term of this patent is extended or adjusted under 35 U.S.C. 154(b) by 445 days.

(21) Appl. No.: 17/520,149

(22) Filed: Nov. 5, 2021

(65) Prior Publication Data

US 2022/0142543 A1    May 12, 2022

(30) Foreign Application Priority Data

Nov. 10, 2020   (DE) .......................... 102020214076.6

(51) Int. Cl.
*A61B 5/263*   (2021.01)
*C01G 15/00*   (2006.01)
*C23C 18/12*   (2006.01)

(52) U.S. Cl.
CPC .............. *A61B 5/263* (2021.01); *C01G 15/00* (2013.01); *C23C 18/1216* (2013.01); *A61B 2562/125* (2013.01)

(58) Field of Classification Search
CPC .. A61B 5/263; A61B 2562/125; C01G 15/00; C23C 18/08; C23C 18/1216; C23C 18/1225; C23C 18/125; C23C 18/1254; C23C 18/1279; C23C 18/1283; C23C 18/1291; Y10T 29/49002
See application file for complete search history.

(56) References Cited

U.S. PATENT DOCUMENTS

| | | | | |
|---|---|---|---|---|
| 4,331,528 A | * | 5/1982 | Beer | ...................... C25B 11/093 148/273 |
| 4,528,084 A | * | 7/1985 | Beer | ...................... C25B 11/093 427/126.3 |
| 4,721,551 A | * | 1/1988 | Byers | ...................... C25D 7/00 205/264 |

(Continued)

FOREIGN PATENT DOCUMENTS

| | | |
|---|---|---|
| EP | 3940110 A1 | 1/2022 |
| JP | 3621148 B2 * | 2/2005 |

(Continued)

OTHER PUBLICATIONS

JP-3621148 translation from Fit database (Year: 2024).*

(Continued)

*Primary Examiner* — Jeffrey T Carley
*Assistant Examiner* — Joshua D Anderson
(74) *Attorney, Agent, or Firm* — Dicke, Billig & Czaja, PLLC

(57) ABSTRACT

The invention relates to a method for producing a medical electrode, comprising the following steps: (i) providing a substrate; (ii) applying a composition onto the substrate, wherein the composition comprises (a) a non-aqueous solvent and (b) an organic iridium complex compound dissolved in the solvent; (iii) heating the composition, and thereby forming a noble metal layer on the substrate.

15 Claims, 1 Drawing Sheet

(56) References Cited

U.S. PATENT DOCUMENTS

| | | | |
|---|---|---|---|
| 5,156,726 A * | 10/1992 | Nakada | C25B 11/093 |
| | | | 204/290.09 |
| 5,696,384 A * | 12/1997 | Ogi | C23C 16/18 |
| | | | 257/E21.174 |
| 5,741,883 A | 4/1998 | Bryant | |
| 5,746,928 A * | 5/1998 | Yen | H01L 21/6833 |
| | | | 134/1.1 |
| 6,048,959 A | 4/2000 | Bryant | |
| 6,686,437 B2 | 2/2004 | Buchman et al. | |
| 6,852,828 B2 | 2/2005 | Scott | |
| 9,799,837 B2 * | 10/2017 | Nagayama | C07F 15/0033 |
| 2002/0190727 A1 | 12/2002 | Morimoto | |
| 2007/0292744 A1 | 12/2007 | Lopez et al. | |
| 2011/0140703 A1 * | 6/2011 | Chiao | G01N 27/403 |
| | | | 324/438 |
| 2014/0322631 A1 | 10/2014 | Klose-Schubert et al. | |
| 2014/0326482 A1 | 11/2014 | Thanawala et al. | |
| 2015/0021194 A1 * | 1/2015 | Sheehan | C25B 11/051 |
| | | | 560/231 |
| 2015/0253280 A1 | 9/2015 | Liu et al. | |
| 2016/0108530 A1 | 4/2016 | Masel et al. | |
| 2017/0187042 A1 | 6/2017 | Jang et al. | |
| 2017/0207464 A1 | 7/2017 | Gyenge et al. | |
| 2019/0016129 A1 | 1/2019 | Takebayashi et al. | |
| 2019/0161868 A1 | 5/2019 | Jang et al. | |
| 2020/0087164 A1 | 3/2020 | Boissiere et al. | |

FOREIGN PATENT DOCUMENTS

| | | | |
|---|---|---|---|
| WO | 20100146475 | 12/2010 | |
| WO | WO-2011073149 A1 * | 6/2011 | C07D 307/91 |
| WO | 2021/058154 | 4/2021 | |
| WO | 2021/259505 | 12/2021 | |

OTHER PUBLICATIONS

WO 2011073149 translation from FIT database (Year: 2024).*

Reichardt, "Empirical Parameters of Solvent Polarity as Linear Free-Energy Relationships" Angew Chem Int Ed Engl 18, pp. 98-110 (1979).

Meyer et al., "Electrodeposited Iridium Oxide for Neural Stimulation and Recording Electrodes" IEEE Transactions on Neural Systems and Rehabilitation Engineering, vol. 9, No. 1, pp. 2-11, Mar. 2001.

Cogan et al., "In Vitro Comparison of the Charge-Injection Limits of Activated Iridium Oxide (AIROF) and Platinum-Iridium Microelectrodes", IEEE Transactions on Biomedical Engineering, vol. 52, No. 9, pp. 1612-1614, Sep. 2005.

Nguyen et al. "Sol-Gel Deposition of Iridium Oxide for Biomedical Micro-Devices", Sensors 15, pp. 4212-4228, 2015.

Cogan, Stuart F., "Electroplated Iridium Oxide EIROF—Product Information and Properties" (EIROF information sheet downloaded from EIC Laboratories, www.EIClabs.com/resbiomed.htm (2 pages) (Copyright © 2004 EIC Laboratories, Inc.).

Cogan et al., "Sputtered iridium oxide films (SIROFs) for neural stimulation electrodes", Conf Proc IEEE Eng Med Biol Soc, 6, pp. 4153-4156, 2004.

Wilks et al., "Non-clinical and Pre-clinical Testing to Demonstrate Safety of the Barostim Neo Electrode for Activation of Carotid Baroreceptors in Chronic Human Implants", Frontiers in Neuroscience, vol. 11, article 438, pp. 1-17, Aug. 2017.

Negi et al., "Morphology and Electrochemical Properties of Activated and Sputtered Iridium Oxide Films for Functional Electrostimulation", Journal of Sensor Technology, 2, pp. 138-147, 2012.

* cited by examiner

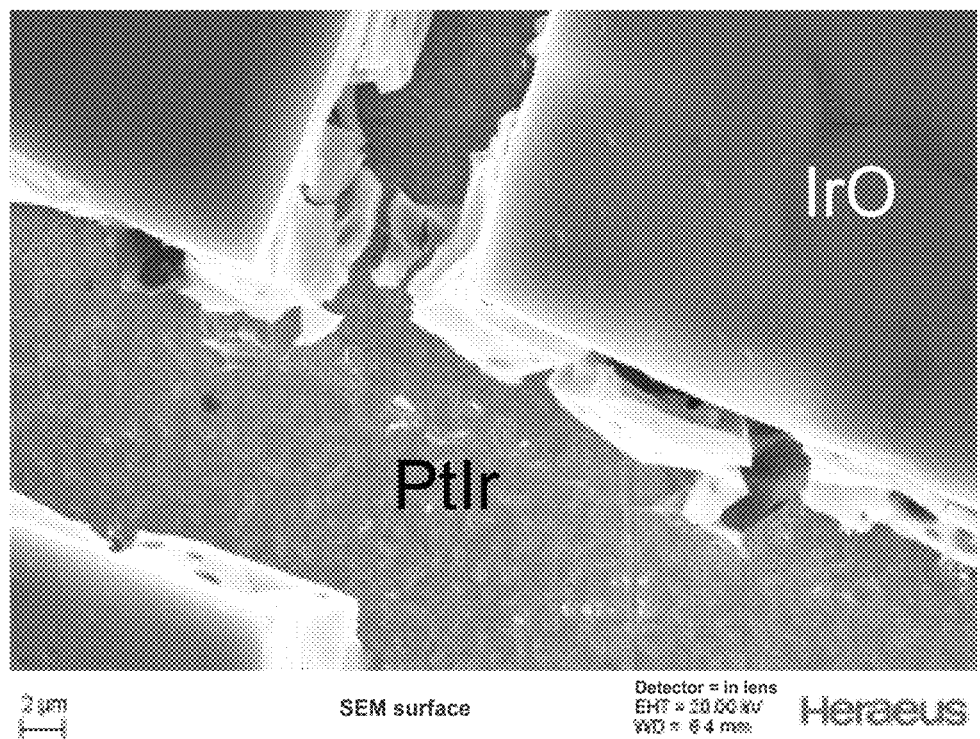

PRODUCTION METHOD FOR NOBLE METAL ELECTRODES

FIELD OF THE INVENTION

The present invention is in the field of medical technology and relates to a method for producing a medical electrode, and to medical electrodes produced by the method.

PRIOR ART

Medical electrodes comprising an iridium oxide coating are described in US20140326482A1, for example. Vacuum-based techniques are usually used to coat medical electrodes with iridium oxide. These techniques are complex, expensive and do not allow maskless location-selective coating.

OBJECT OF THE INVENTION

The present invention provides methods for producing a medical electrode, which offer a number of technical advantages. For example, structures can be produced from iridium oxide in a simple and/or cost-effective manner. These structures can also be applied to temperature-sensitive substrates. In addition, the iridium oxide layers can be applied in almost any desired shape, without the need for a specially made mask.

PREFERRED EMBODIMENTS

The object of the present invention is to solve one or more of the problems illustrated above and further problems of the prior art. The invention is described hereinafter by way of example using the following preferred embodiments. However, it is not limited to these embodiments.
1. Method for producing a medical electrode coated with iridium oxide, comprising the following steps:
   (i) providing a medical electrode having an electrode surface;
   (ii) applying a liquid composition to the electrode surface, the composition comprising an organic iridium complex compound; and
   (iii) heating the composition in an oxygen-containing atmosphere, thereby forming an iridium oxide layer on the electrode surface.
2. Method according to Embodiment 1, wherein the solubility of the organic iridium complex compound in propylene glycol monopropyl ether at 25° C. and 1013 hPa is preferably at least 1% by mass, more preferably at least 2, 3, 4, 5, or 10% by mass, based on the total mass of the composition.
3. Method according to Embodiment 1 or 2, wherein the composition comprises a non-aqueous solvent.
4. Method according to any one of the preceding embodiments, wherein step (iii) is carried out above the decomposition temperature of the iridium complex compound but below the lowest melting or decomposition temperature of a material of the electrode surface.
5. Method according to any one of the preceding embodiments, wherein the electrode surface comprises a metal, a ceramic, or a plastic, or consists at least in sections of metal, ceramic, or plastic.
6. Method according to any one of the preceding embodiments, wherein the composition is applied using one of the following methods: printing, dip coating, spray coating, spin coating, knife coating, application by means of a saturated application tool.
7. Method according to any one of the preceding embodiments, wherein the heating, and thereby the formation of an iridium oxide layer, is carried out at a temperature of less than 1000° C., 900° C., 800° C., 700° C., 600° C., 500° C., 400° C., 300° C., 250° C., 200° C., or less than 150° C.
8. Method according to any one of the preceding embodiments, wherein the heating, and thereby the formation of an iridium oxide layer, is carried out at a pressure of approximately 1000 hPa.
9. Method according to any one of the preceding embodiments, wherein the application of the composition to the electrode surface takes place selectively in the shape of a predetermined pattern so that the formed iridium oxide layer is given the shape of the predetermined pattern.
10. Method according to any one of the preceding embodiments, wherein steps (ii) and (iii) are repeated once or several times in order to incrementally build up a thicker iridium oxide layer.
11. Method according to any one of the preceding embodiments, wherein the composition comprises an iridium complex comprising diolefin and C6-C18 monocarboxylate ligands of type $[LIr[O(CO)R1]]_m$, where L denotes a compound acting as a diolefin ligand, where —O(CO)R1 and —O(CO)R2 denote identical or different non-aromatic C6-C18 monocarboxylic acid radicals, and where m is an integer $\geq 2$.
12. Method according to Embodiment 11, wherein L is cyclooctadiene or norbornadiene, where n is 1 or 2, where m is 2, and where R1 is a non-aromatic C5-C17 hydrocarbon radical.
13. Method according to any one of the preceding embodiments, wherein the iridium oxide layer has a thickness of 50 nm to 5 µm, preferably 200 nm to 2 µm, more preferably 300 nm to 1 µm.
14. Coated medical electrode produced by a method according to any one of the preceding embodiments.
15. Medical electrode comprising a printed iridium oxide layer.
16. Medical electrode comprising a flexible carrier substrate coated with an iridium oxide layer.

DETAILED DESCRIPTION OF THE INVENTION

Brief Description of the Drawings

FIG. 1 shows a scanning electron microscope image of an iridium oxide layer according to the invention.

In principle, for the embodiments described herein, the elements of which "have" or "comprise" a particular feature (e.g., a material), a further embodiment is always considered in which the element in question consists of that feature alone, i.e., comprises no further components. The word "comprise" or "comprising" is used herein synonymously with the word "have" or "having." If an element is referred to in the singular in an embodiment, an embodiment is also being considered in which several of these elements are present.

Unless otherwise indicated or clearly ruled out by the context, it is possible in principle, and is hereby contemplated, that features of different aspects and embodiments may also be present in the other aspects and embodiments described herein.

The present invention relates to iridium-containing compositions as such, and to their use for producing medical electrodes. Accordingly, it is considered, in principle, that all features described herein in connection with a method can also be used per se for the products described herein, for example for an electrode coated with iridium oxide, an iridium complex compound according to the invention, and a composition containing such an iridium complex compound, and vice versa. Only for reasons of a more succinct presentation are all such considered combinations not explicitly listed in detail in all instances. Technical solutions which are known to be equivalent to the features described herein are also intended to be encompassed in principle by the scope of the invention.

A first aspect of the invention relates to a method for producing a medical electrode, comprising the following steps:
(i) providing a medical electrode having an electrode surface;
(ii) applying a liquid composition to the electrode surface, the composition comprising an organic iridium complex compound; and
(iii) heating the composition in an oxygen-containing atmosphere, thereby forming an iridium oxide layer on the electrode surface.

Here, the solubility of the organic iridium complex compound in propylene glycol monopropyl ether at 25° C. and 1013 hPa is preferably at least 1% by mass, more preferably at least 2, 3, 4, 5, or 10% by mass, in each case based on the total mass of the composition.

When solubility herein refers to propylene glycol monopropyl ether or another particular solvent, or several different solvents, this does not necessarily mean that the composition described herein comprises this solvent or these several solvents. In principle, it should merely be emphasized that iridium complexes with the described solubilities are particularly suitable for use in the compositions, uses, methods according to the invention and products produced thereby. In particular, good solubility in various solvents can be advantageous for the use of certain coating methods. For example, iridium complexes that are readily soluble in organic solvents are advantageous for use in printing methods, for example inkjet printing methods.

The organic iridium complex compound preferably has a low content of halogens, for example it contains less than 25% by weight, more preferably less than 20, 15 or 10% by weight of halogens, based on the total weight of the complex compound. In one embodiment, the iridium complex compound does not comprise a structure Ir—X, where X is a halogen, i.e., the compound does not comprise any direct molecular bond between iridium and a halogen.

In one embodiment, the iridium complex compound is uncharged, i.e., it has no positive or negative overall charge. In one embodiment, the iridium complex compound is pH neutral, i.e., it does not lead to an increase in the proton concentration upon contact with an aqueous solution. In one embodiment, the iridium complex compound is a non-ionic complex.

In one embodiment, the iridium complex compound is readily soluble in both polar and non-polar solvents. In one embodiment, the iridium complex compound is readily soluble in solvents of medium polarity. Solvents of medium polarity are, for example, short-chain ethers and alcohols, as well as glycol ethers.

In one embodiment, the solubility of the organic iridium complex compound in ethanol at 25° C. and 1013 hPa is at least 1, preferably at least 2, 3, 4, 5, or at least 10% by mass.

In one embodiment, the solubility of the organic iridium complex compound in toluene at 25° C. and 1013 hPa is at least 1, preferably at least 2, 3, 4, 5, or at least 10% by mass.

In one embodiment, the solubility of the organic iridium complex compound in a solvent mixture comprising eight parts of ethanol and two parts of water at 25° C. and 1013 hPa is at least 1, preferably at least 2, 3, 4, 5, or at least 10% by mass.

In one embodiment, the solubility of the organic iridium complex compound in ethanol is at least 1% by mass and in n-hexane is at least 1% by mass.

In one embodiment, the solubility of the organic iridium complex compound in ethanol is at least 2% by mass and in n-hexane is at least 2% by mass.

In one embodiment, the solubility of the organic iridium complex compound in ethanol is at least 3% by mass and in n-hexane is at least 3% by mass.

In one embodiment, the solubility of the organic iridium complex compound in ethanol is at least 4% by mass and in n-hexane is at least 4% by mass.

In one embodiment, the solubility of the organic iridium complex compound in ethanol is at least 5% by mass and in n-hexane is at least 5% by mass.

In one embodiment, the solubility of the organic iridium complex compound in ethanol is at least 10% by mass and in n-hexane is at least 10% by mass.

In one embodiment, the solubility of the organic iridium complex compound in ethanol is at least 2% by mass and in n-hexane is at least 1% by mass.

In one embodiment, the solubility of the organic iridium complex compound in ethanol is at least 2% by mass and in n-hexane is at least 3% by mass.

In one embodiment, the solubility of the organic iridium complex compound in ethanol is at least 2% by mass and in n-hexane is at least 4% by mass.

In one embodiment, the solubility of the organic iridium complex compound in ethanol is at least 2% by mass and in n-hexane is at least 5% by mass.

In one embodiment, the solubility of the organic iridium complex compound in ethanol is at least 2% by mass and in n-hexane is at least 10% by mass.

In one embodiment, the solubility of the organic iridium complex compound in propylene glycol monopropyl ether is at least 1% by mass, in ethanol is at least 1% by mass, and in n-hexane is at least 1% by mass.

In one embodiment, the solubility of the organic iridium complex compound in propylene glycol monopropyl ether is at least 1% by mass, in ethanol is at least 2% by mass, and in n-hexane is at least 2% by mass.

In one embodiment, the solubility of the organic iridium complex compound in propylene glycol monopropyl ether is at least 1% by mass, in ethanol is at least 3% by mass, and in n-hexane is at least 3% by mass.

In one embodiment, the solubility of the organic iridium complex compound in propylene glycol monopropyl ether is at least 1% by mass, in ethanol is at least 4% by mass, and in n-hexane is at least 4% by mass.

In one embodiment, the solubility of the organic iridium complex compound in propylene glycol monopropyl ether is at least 1% by mass, in ethanol is at least 5% by mass, and in n-hexane is at least 5% by mass.

In one embodiment, the solubility of the organic iridium complex compound in propylene glycol monopropyl ether is at least 1% by mass, in ethanol is at least 10% by mass, and in n-hexane is at least 10% by mass.

In one embodiment, the solubility of the organic iridium complex compound in propylene glycol monopropyl ether is at least 1% by mass, in ethanol is at least 2% by mass, and in n-hexane is at least 1% by mass.

In one embodiment, the solubility of the organic iridium complex compound in propylene glycol monopropyl ether is at least 1% by mass, in ethanol is at least 2% by mass, and in n-hexane is at least 3% by mass.

In one embodiment, the solubility of the organic iridium complex compound in propylene glycol monopropyl ether is at least 1% by mass, in ethanol is at least 2% by mass, and in n-hexane is at least 4% by mass.

In one embodiment, the solubility of the organic iridium complex compound in propylene glycol monopropyl ether is at least 1% by mass, in ethanol is at least 2% by mass, and in n-hexane is at least 5% by mass.

In one embodiment, the solubility of the organic iridium complex compound in propylene glycol monopropyl ether is at least 1% by mass, in ethanol is at least 2% by mass, and in n-hexane is at least 10% by mass.

In some embodiments, the organic iridium complex compound is virtually indefinitely soluble in the solvent or in any one of the solvents mentioned herein. This means that the iridium complex compound and the solvent are miscible with each other in any proportion.

In one embodiment, the organic iridium complex compound is miscible in any proportion with a solvent selected from the group consisting of 1,5-cyclooctadiene (also referred to herein as COD), neodecanoic acid, norbornadiene, and cyclohexanoic acid.

The solubility of the iridium complex compound in the solvent can be determined, for example, by gradually adding the solvent in a small amount, i.e., titrating, at 25° C. and 1013 hPa to a defined amount of the iridium complex compound until all the solids are dissolved. In the process, the mixture of iridium complex compound and solvent is stirred continuously so that it is uniformly mixed.

The solvent can be any suitable liquid substance in which the organic iridium complex compound can be dissolved. The solvent can contain several chemical substances, i.e., the solvent can also be a mixture of solvents. In one embodiment, the solvent is a non-aqueous solvent. "Non-aqueous solvent" herein shall be understood to mean that the solvent comprises at least one liquid substance in which the organic iridium complex compound is soluble, wherein this liquid substance is not water or an aqueous solution of inorganic substances. The solvent accordingly comprises at least one substance, with the exception of water, which is liquid at 25° C. and 1013 hPa, in which the organic iridium complex compound is soluble.

A suitable solvent can be selected on the basis of the solubility of the iridium complex compound in the solvent, the compatibility with the desired application method, and/or the required wetting properties with respect to the substrate. The solvent itself should preferably not lead to a change in the substrate, for example a chemical reaction with the substrate, or dissolution, softening, or swelling of the substrate. Suitable solvents and solvent mixtures are known in the art and can be selected by simple experiments with respect to the aforementioned properties. Preferred solvents are non-polar substances, for example uncharged organic compounds. These can be pure hydrocarbons or heteroatom-containing compounds, such as heteroalkanes, heteroaromatics, and heteroalkenes.

Examples of organic solvents according to the invention include aliphates and cycloaliphates, each having 6 to 12 carbon atoms; halocarbons, such as di-, tri-, and tetrachloromethane; aromatics; araliphates, such as toluene or xylene; alcohols, such as ethanol, n-propanol, and isopropanol; ethers; glycol ethers, such as mono-C1-C4 alkyl glycol ethers and di-C1-C4 alkyl glycol ethers, for example ethylene glycol mono-C1-C4 alkyl ether, ethylene glycol di-C1-C4 alkyl ether, diethylene glycol mono-C1-C4 alkyl ether, diethylene glycol di-C1-C4 alkyl ether, propylene glycol mono-C1-C4 alkyl ether, propylene glycol di-C1-C4 alkyl ether, dipropylene glycol mono-C1-C4 alkyl ether, and dipropylene glycol di-C1-C4 alkyl ether; esters having 2 to 12 carbon atoms; and ketones, such as acetone, methyl ethyl ketone, methyl isobutyl ketone, and cyclohexanone.

In certain embodiments, the solvent is a non-aqueous solvent usable for inkjet applications. In some embodiments, the solvent is compatible with the coating of plastics, for example PEEK or polyimides, which are described in more detail below. In some embodiments, the solvent has good wetting properties with respect to plastics. In some embodiments, the solvent has good wetting properties with respect to metals, such as platinum or platinum iridium alloys. In some embodiments, the solvent has a medium polarity. For example, the dipole moment of the solvent can be 1 to 10; 1 to 8; 1 to 5; or 2 to $4 \times 10^{-30}$ Cm.

In one embodiment, the solvent is a protic solvent. In one embodiment, the solvent is an aprotic solvent.

In one embodiment, the ET30 value of the solvent is 30 to 52 kcal/mol, 30 to 50 kcal/mol, or 35 to 45 kcal/mol. In one embodiment, the ET30 value of the solvent is 120 to 240 kJ/mol, 125 to 220 kJ/mol, or 160 to 200 kJ/mol. The $E_T(30)$ value, also referred to as the "ET30 value" herein, of a solvent is defined as the transition energy of the longest-wave VIS/NIR absorption bands in a solution comprising the negatively solvatochromic Reichardt's dye (Betaine 30) at normal conditions defined in kcal/mol (REICHARDT, *Angew Chem Int Ed Engl* 18, 98-110 (1979); C. REICHARDT, Solvents and Solvent Effects in Organic Chemistry, Wiley-VCH, Weinheim, 2011; C. REICHARDT, Solvent Effects in Organic Chemistry, Verlag Chemie, Weinheim, 1973; all hereby fully incorporated by reference). Some exemplary solvents and their ET(30) values are shown below in Table 1.

TABLE 1

Exemplary solvents and their $E_T(30)$ values according to REICHARDT, *Angew Chem Int Ed Engl* 18, 98-110 (1979).

| Solvent | $E_T(30)$ value [kcal/mol] |
|---|---|
| Ethanol | 51.9 |
| 1-propanol | 48.6 |
| 2-propanol | 41.1 |
| Dichloromethane | 50.7 |
| Diethylene glycol diethyl ether | 37.9 |
| n-octane | 31.1 |
| n-hexane | 30.9 |

In one embodiment, heating the composition causes the organic iridium complex compound to decompose so that a pure iridium or iridium oxide layer remains on the substrate. In one embodiment, the heating causes the solvent to evaporate. In one embodiment, the solvent is evaporated as a result of the heating, and the organic iridium complex compound is completely decomposed. In one embodiment, essentially no further component of the composition remains on the substrate, except for the pure iridium or iridium oxide, after the composition has been heated.

The composition can furthermore also contain an additive, as described in more detail below.

The composition is preferably liquid and has a lower viscosity, for example a viscosity of less than 100, less than 50, or less than 40 cP at 20° C. and 1013 hPa. The composition is preferably not a sol-gel. The viscosity of the composition can be determined by rotational viscometry according to the plate-plate measuring principle, using a plate diameter of 25 mm, measuring gap of 1 mm, shear rate of 36 min$^{-1}$, the viscosity value being determined after a measuring time of 2 minutes.

The composition is preferably a clear solution, i.e., a liquid that is free of colloids or precipitates. The composition preferably comprises only a single phase, i.e., the individual components of the composition are completely homogeneously mixed.

The organic iridium complex compound comprises at least one central iridium atom, which is complexed by one or more organic ligands by one or more free electrode pairs.

The organic iridium complex compound is preferably soluble in a solvent, for example an organic solvent or solvent mixture suitable for inkjet printing methods. For this purpose, the organic iridium complex compound can comprise a hydrocarbon radical having 7 to 17 carbon atoms, preferably 7 to 10 carbon atoms. The organic iridium complex compound can also comprise several such hydrocarbon radicals.

The organic iridium complex compound preferably does not comprise any halogens.

The organic iridium complex compound can, for example, comprise an iridium complex of type [LIr[O(CO)R1]]$_m$, where L denotes a compound acting as a diolefin ligand, where —O(CO)R1 and —O(CO)R2 denote identical or different non-aromatic C6-C18 monocarboxylic acid radicals, and where m is an integer ≥2.

In one embodiment, the substrate can comprise a metal, a ceramic, or a plastic, or consist of metal, ceramic, or plastic. Examples of suitable plastics are, for example, PTFE, PU, ETFE, PI, PET, PE, or PEEK. The substrate can be a flat substrate, for example made of plastic, or a metal wire. Examples of polyimides (PI) are Vespel (CAS no.: 62929-02-6) and Kapton (poly(4,4'-oxydiphenylene-pyromellitimide). Polyimides based on biphenyl dianhydride and p-phenylenediamine (BPDA and PPD), for example PI2611 (DuPont) or U-Varnish-S (UBE), as well as polyimides based on 4,4'-oxydiphthalic acid anhydride and 3,4,3',4'-biphenyltetracarboxylic acid dianhydride, as described in U.S. Pat. Nos. 5,741,883, 6,048,959, 6,852,828, and 6,686437 (all hereby fully incorporated by reference) are characterized by good biocompatibility. Further examples are polymers that can be prepared from 4,4'-oxydiphthalic acid anhydride and 3,4,3',4'-biphenyltetracarboxylic acid dianhydride, and one of 3,4'-oxydianiline. Another example is the polymer MP-1 (M.M.A. Tech Ltd., Nahariya 2201202, Israel). The substrate can be a flexible substrate, for example a film comprising one of the aforementioned plastics or consisting thereof. The substrate can preferably be a so-called flex PCB, i.e., a film-based printed circuit board. Such substrates can, for example, comprise liquid crystal polymers (LCPs), which are available, for example, from Tech Etch Inc., 45 Aldrin Road, Plymouth, MA 02360, USA or from DYCONEX AG, CH-8303 Bassersdorf, Switzerland. Further examples of liquid crystal polymers are RTP 3499-3 X 113393 A available from RTP Company and VECTRA® E840i LDS available from Ticon. The substrate is preferably biocompatible. The substrate is preferably suitable for attachment to or implantation in the human body. Examples of biocompatible metals are platinum, titanium, gold, and platinum iridium alloys.

The substrate can optionally be cleaned and/or pre-treated before the composition is applied. For example, the substrate can be roughened by shot blasting. In one embodiment, the composition is applied directly to the substrate, i.e., there is no further layer between the substrate and the composition.

In particular, the use of adhesion promoters, for example adhesion-promoting organic substances (primers) or an additional layer of another metal, such as titanium, chromium, or nickel, can preferably be dispensed with.

The composition can be applied by various methods, for example by dipping (also referred to as dip coating), spray application, printing, stamping, paintbrush application, brush application, application using felt, and application using a cloth. Stamping also includes the methods known in the art as "pad printing" and "micro-contact printing."

In one embodiment, the composition is selectively applied to the substrate in the shape of a predetermined pattern so that the layer comprising the formed iridium is given the shape of the predetermined pattern. Such a pattern can, for example, comprise elements having different structure widths, which can, due to their respective different shape, serve for example as contact elements, conductor tracks, or active electrode surfaces for receiving or emitting an electrical signal. For example, the composition is applied for this purpose by a structuring method, for example an inkjet printing method. A structuring method can comprise a selective application of the composition to the substrate. This is also referred to in the art as a bottom-up method. This can be done, for example, by a spatially resolved control of an application element, for example a nozzle, or by using a mask. In one embodiment, the composition is first applied areally, and then removed using an ablation method, for example laser ablation, in order to produce a structured layer comprising iridium. This is also referred to in the art as a top-down method. In principle, any bottom-up method or top-down method known in the art that is suitable for applying, as described herein, a liquid and creating a structured layer comprising iridium on a substrate can be used. In one embodiment, several structured layers comprising iridium are applied to the substrate, wherein application methods that are the same as or different than those described above can be used.

In some embodiments, the method is carried out at a low temperature. In particular, the heating of the composition to form an iridium oxide layer that is as pure as possible can be carried out at a temperature of less than 1000° C., 900° C., 800° C., 700° C., 600° C., 500° C., 400° C., 300° C., 250° C., 200° C., or less than 150° C. The method is particularly preferably carried out overall at a temperature of less than 300° C., i.e., the substrate and the composition are not heated above a temperature of 300° C. In this way, temperature-sensitive substrates can also be coated with an iridium oxide layer.

The method can preferably take place without the application of a vacuum. For example, the method can be carried out at a pressure of approximately 1000 hPa, for example at normal pressure, i.e., 1013 hPa.

Steps (ii) and (iii) can be repeated once or several times in order to incrementally build up a thicker iridium oxide layer. For this purpose, steps (ii) and (iii) are preferably carried out repeatedly in an alternating sequence; i.e., after the formation of a first iridium oxide layer by heating, the liquid composition is applied a second time, which in turn is heated in order to form a second iridium oxide layer on top of the first iridium oxide layer.

A composition according to the invention can, for example, comprise the following components:
(A) 30 to 90% by weight of at least one organic solvent;
(B) 10 to 70% by weight of at least one iridium complex comprising diolefin and C6-C18 monocarboxylate ligands of type [LIr[O(CO)R1]]m, where L denotes a compound acting as a diolefin ligand, where —O(CO)

R1 and —O(CO)R2 denote identical or different non-aromatic C6-C18 monocarboxylic acid radicals, and where m is an integer ≥2; and (C) 0 to 10% by weight of at least one additive.

In one embodiment, the composition is substantially composed of the aforementioned components A, B, and optionally C.

In such a composition, component (B) is present dissolved in component (A). If the optional component (C) is present in the composition according to the invention, this component (C) is also preferably present dissolved in component (A). In other words, in the absence of the optional component (C), the composition according to the invention is an organic solution, more precisely, a genuine, i.e., non-colloidal, organic solution; the same applies when the optional component (C) is present in the preferred form, i.e., in the form dissolved in component (A).

The composition according to the invention can contain, for example, 30 to 90% by weight of at least one organic solvent (A). The organic solvent(s) can be selected from a plurality of common organic solvents since the iridium complexes have good to unlimited solubility in such organic solvents. Advantageously, the organic solvent(s) is/are substantially volatile under the processing conditions of the composition according to the invention; this applies in particular to the stage after the composition according to the invention has been applied to a substrate. In general, the boiling points of the organic solvent(s) are in the range of 50 to 200° C. or higher, for example 50 to 300° C. Examples of organic solvents (A) include aliphates and cycloaliphates, each having 6 to 12 carbon atoms; halocarbons, such as di-, tri-, and tetrachloromethane; aromatics; araliphates, such as toluene or xylene; alcohols, such as ethanol, n-propanol, and isopropanol; ethers; glycol ethers, such as mono-C1-C4 alkyl glycol ethers and di-C1-C4 alkyl glycol ethers, for example ethylene glycol mono-C1-C4 alkyl ether, ethylene glycol di-C1-C4 alkyl ether, diethylene glycol mono-C1-C4 alkyl ether, diethylene glycol di-C1-C4 alkyl ether, propylene glycol mono-C1-C4 alkyl ether, propylene glycol di-C1-C4 alkyl ether, dipropylene glycol mono-C1-C4 alkyl ether, and dipropylene glycol di-C1-C4 alkyl ether; esters having 2 to 12 carbon atoms; and ketones, such as acetone, methyl ethyl ketone, methyl isobutyl ketone, and cyclohexanone.

Araliphates, such as toluene or xylene; alcohols, such as ethanol, n-propanol, and isopropanol; and glycol ethers, such as mono-C1-C4 alkyl glycol ethers and di-C1-C4 alkyl glycol ethers, for example ethylene glycol mono-C1-C4 alkyl ethers; ethylene glycol di-C1-C4 alkyl ether, diethylene glycol mono-C1-C4 alkyl ether, diethylene glycol di-C1-C4 alkyl ether, propylene glycol mono-C1-C4 alkyl ether, propylene glycol di-C1-C4 alkyl ether, dipropylene glycol mono-C1-C4 alkyl ether, and dipropylene glycol di-C1-C4 alkyl ether are preferred.

Component (A) or the at least one organic solvent (A) consists particularly preferably of at least one alcohol, specifically at least one of the alcohols mentioned by way of example, and/or of at least one glycol ether, specifically at least one of the glycol ethers mentioned by way of example. Corresponding mixtures of 30 to 70% by weight alcohol and the fraction of glycol ether missing to make up 100% by weight are particularly preferred as component (A).

As already stated, the compositions according to the invention preferably contain, as component (B), 10 to 70% by weight of at least one iridium complex comprising diolefin and C6-C18 monocarboxylate ligands of type [LIr[O(CO)R1]]$_m$, where L denotes a compound acting as a diolefin ligand, where —O(CO)R1 and —O(CO)R2 denote identical or different non-aromatic C6-C18 monocarboxylic acid radicals, in each case preferably with the exception of a phenylacetic acid radical, and where m is an integer ≥2.

The iridium content of a composition according to the invention originating from the at least one iridium complex can, for example, be in the range of 2.5 to 25% by weight, based on the total mass of the composition.

In a preferred embodiment, bi- or polynuclear iridium complexes of type [LIr[O(CO)R1]]$_m$, L denotes a compound acting as a diolefin ligand; m denotes 2, 3, 4, or 5, preferably 2; and —O(CO)R1 denotes a non-aromatic C6-C18 monocarboxylic acid radical, preferably with the exception of a phenylacetic acid radical.

Said iridium complexes can be present in the compositions according to the invention in individualized form, but also in combined form, i.e., alone or also as a mixture of several different species. Iridium complexes can thus be present in the compositions according to the invention in individualized or combined form, i.e., alone or as a mixture of several different species, in each case of type [LIr[O(CO)R1]]$_m$. In other words, component (B) can be represented in only one individual form (individualized) or in more than one individual form (combined). The term "individual form" used here in this context refers to the formula type with the specific index m; for example, [LIr[O(CO)R1]]$_2$ is the individual form of the general type [LIr[O(CO)R1]]$_m$, where m=2.

As an alternative or in addition to the Ir complexes, the compositions according to the invention can also comprise platinum compounds of type [LPt[O(CO)R1]X]$_n$. Such platinum compounds are disclosed in the PCT application with application number PCT/EP2020/068465.

As an alternative or in addition to the Ir complexes, the compositions according to the invention can also comprise noble metal complexes of type [LPd[O(CO)R1]X]$_n$, [LRh[O(CO)R1]]$_m$. Such noble metal complexes are disclosed in the EP application with application number 20185479.1 and the PCT application with application number PCT/EP2020/069185.

Examples of diolefins or compounds of type L that are capable of acting as diolefin ligands include hydrocarbons, such as COD (1,5-cyclooctadiene), NBD (norbornadiene), COT (cyclooctatetraene), and 1,5-hexadiene, in particular COD and NBD. These are preferably pure hydrocarbons; however, the presence of heteroatoms, for example also in the form of functional groups, is also possible.

X can denote bromide, chloride, iodide, or —O(CO)R2; it preferably denotes chloride or —O(CO)R2, in particular —O(CO)R2.

The non-aromatic monocarboxylic acid radicals —O(CO)R1 and —O(CO)R2 in each case denote identical or different non-aromatic C6-C18 monocarboxylic acid radicals, in each case preferably with the exception of a phenylacetic acid radical. The term "non-aromatic" used in this context excludes purely aromatic monocarboxylic acid radicals but not araliphatic monocarboxylic acid radicals whose carboxyl function(s) is/are bound to aliphatic carbon. —O(CO)R1 and also —O(CO)R2 preferably do not denote a phenylacetic acid radical. Preferably, —O(CO)R1 and —O(CO)R2 denote identical non-aromatic C6-C18-monocarboxylic acid radicals but preferably no phenylacetic acid radicals. Among the non-aromatic C6-C18 monocarboxylic acid radicals, monocarboxylic acid radicals having 8 to 18 carbon atoms, i.e., non-aromatic C8-C18 monocarboxylic acid radicals, are preferred.

Examples of non-aromatic C6-C18- or the preferred C8-C18-monocarboxylic acids comprising the radicals —O(CO)R1 or —O(CO)R2 include the isomeric hexanoic acids, including n-hexanoic acid; the isomeric heptanoic acids, including n-heptanoic acid; the isomeric octanoic acids, including n-octanoic acid and 2-ethylhexanoic acid; the isomeric nonanoic acids, including n-nonanoic acid; and the isomeric decanoic acids, including n-decanoic acid, to name just a few examples. Not only linear representatives but also those having branches and/or cyclic structures, such as 2-ethylhexanoic acid, cyclohexanecarboxylic acid, and neodecanoic acid, are included. The R1 and R2 radicals bound in each case to a carboxyl group comprise 5 to 17 and 7 to 17 carbon atoms, respectively; benzyl radicals are preferably excluded in each case.

Preferred examples of iridium complexes include [(COD)Ir[O(CO)R1]]$_m$ and [(NBD)Ir[O(CO)R1]]$_m$, where m is 2, and where R1 denotes a non-aromatic C5-C17 hydrocarbon radical, in each case preferably with the exception of benzyl.

The iridium complexes can be easily prepared by ligand exchange, in particular without using silver salts of carboxylic acid. The production method comprises mixing or suspending or emulsifying a two-phase system. The one phase here comprises a reactant of the type [LIrX]$_2$, in each case with X selected from bromide, chloride, and iodide, preferably chloride, either as such or preferably in the form of an at least substantially water-immiscible organic solution of such a reactant. Examples of organic solvents that are suitable for producing such an organic solution and at least substantially water-immiscible also include oxygen-containing solvents, for example corresponding water-immiscible ketones, esters, and ethers, in addition to aromatics and chlorinated hydrocarbons, such as toluene, xylene, di-, tri-, and tetrachloromethane. In contrast, the other phase comprises, for example, an aqueous solution of alkali salt (in particular sodium or potassium salt) and/or magnesium salt of a C6-C18 monocarboxylic acid of type R1COOH and optionally additionally of type R2COOH. The selection of the type of monocarboxylic acid salt or salts depends on the type of iridium complex to be produced or the combination of iridium complexes to be produced. The two phases are intensively mixed, for example by shaking and/or stirring, thereby forming a suspension or an emulsion. Mixing for the purpose of maintaining the suspension or emulsion state, for example, is carried out for a duration of 0.5 to 24 hours, for example at a temperature in the range of 20 to 50° C. The ligand exchange takes place in the process, wherein the iridium complex or complexes formed dissolves or dissolve in the organic phase, while the alkali X salt or MgX$_2$ salt likewise formed dissolves in the aqueous phase. Upon completion of the suspension or emulsification, organic and aqueous phases are separated from one another. The iridium complex or complexes formed can be obtained from the organic phase and, if necessary, subsequently be purified by means of conventional methods.

An important property, in addition to the aforementioned solubility in common organic solvents, is the comparatively low decomposition temperature of the iridium complex or complexes of component (B), for example already starting at 150° C. to 300° C., often no higher than 250° C. This combination of properties makes it possible to use such iridium complexes as component (B) of the composition according to the invention for producing layers comprising iridium on substrates; in this way, the composition according to the invention represents a covering agent (coating agent), i.e., it is then prepared and usable as a coating agent.

The compositions according to the invention comprise 0 to 10% by weight, preferably 0 to 3% by weight of at least one additive (C). Accordingly, the compositions according to the invention can be additive-free or comprise up to 10% by weight of at least one additive. Examples of additives include wetting additives, rheological additives, defoamers, deaerators, additives for influencing the surface tension, and odorants.

Compositions according to the invention can be produced by simply mixing components (A), (B), and, if desired, (C). The person skilled in the art selects the quantitative ratio of the components, adapted to the respective intended use and/or to the application method used therein.

The compositions according to the invention can be used to produce layers comprising iridium on substrates, in particular also on temperature-sensitive substrates. In particular, the compositions can be used to produce or coat a medical electrode. The compositions according to the invention can first be used for the production of coating layers (coatings), which can subsequently be subjected to thermal decomposition. When working with compositions according to the invention based on iridium complexes of type [LIr[O(CO)R1]]$_n$, substantially corresponding iridium oxide layers or even iridium oxide layers free of the corresponding metallic iridium are formed in the presence of air as the ambient atmosphere. In this respect, the person skilled in the art understands the term "layer comprising iridium" used herein in connection with the production in an oxygen-containing atmosphere to mean a layer substantially, or even exclusively, comprising iridium oxide, or consisting thereof, in short a layer comprising or consisting of iridium oxide. According to the invention, layers comprising iridium oxide obtainable on substrates, or substrate surfaces equipped therewith, in particular medical electrodes, can have improved electrical properties, such as reduced impedance and/or increased charge storage capacity.

As mentioned above, during the thermal treatment, the coating layers decompose, forming layers that comprise iridium, i.e., the coating layers are ultimately converted into layers that comprise iridium or iridium oxide or substantially consist thereof. The invention therefore also relates to a method for producing a medical electrode, comprising the following steps:

(1) applying a coating layer made of a composition according to the invention onto a substrate, and
(2) thermally decomposing the coating layer, forming the layer comprising iridium.

The substrates to be provided with the coating layer in step (1) can be substrates that comprise a wide variety of materials. The substrates can comprise only one or even several materials. In one embodiment, the substrate can comprise a metal, a ceramic, or a plastic, or consist of metal, ceramic, or plastic. Examples of suitable plastics are, for example, PTFE, PU, ETFE, PI, PET, PE, or PEEK. The substrate can be a flat substrate, for example made of plastic, or a metal wire.

Known application methods can be used during the production of the coating layer according to step (1).

A first application method is dip coating. The substrate to be provided with the coating layer or ultimately to be provided with the layer comprising iridium is immersed in the composition according to the invention and then removed again. The content of component (A) during dipping is preferably in the range of 30 to 90% by weight of the composition according to the invention and the content of component (B) is preferably in the range of 10 to 70% by weight.

A second application method is spray coating. The substrate to be provided with the coating layer or ultimately to be provided with the layer comprising iridium is spray-coated with the composition according to the invention, using a conventional spray-coating tool. Examples of spray-coating tools are pneumatic spray guns, airless spray guns, rotary atomizers, or the like. The content of component (A) during spray application is preferably in the range of 50 to 90% by weight of the composition according to the invention and the content of component (B) is preferably in the range of 10 to 50% by weight.

A third application method is printing. The substrate to be provided with the coating layer or ultimately to be provided with the layer comprising iridium is printed with the composition according to the invention. A preferred printing method is inkjet printing; the composition according to the invention here represents a coating agent in the form of an ink. Another preferred printing method is aerosol jet printing. A further printing method is screen printing. The content of component (A) during printing is preferably in the range of 50 to 90% by weight of the composition according to the invention and the content of component (B) is preferably in the range of 10 to 50% by weight.

A fourth application method is the application by means of an application tool saturated with the composition according to the invention, for example a paintbrush, a brush, felt, or a cloth. The composition according to the invention is transferred from the application tool to the substrate to be provided with the coating layer or ultimately to be provided with the layer comprising iridium. The content of component (A) in the case of such an application technique is preferably in the range of 30 to 90% by weight of the composition according to the invention and the content of component (B) is preferably in the range of 10 to 70% by weight.

Further application methods include spin coating and knife coating.

The coating layer that is applied from a composition according to the invention and comprises at least one component (B) can first be dried and partially or completely freed of the organic solvent (A) in the process before it, or the dried residue, is subjected to thermal decomposition, forming the layer comprising iridium.

The thermal treatment taking place for the purpose of thermal decomposition comprises heating to an object temperature above the decomposition temperature of the at least one iridium complex (B). If several different iridium complexes (B) are present, the person skilled in the art selects the object temperature above the decomposition temperature of the iridium complex of type (B) having the highest decomposition temperature. For this purpose, for example, heating is generally carried out briefly to an object temperature above the decomposition temperature, for example to an object temperature in the range of >150° C. to 200° C. or >150° C. to 250° C. or higher, for example to 1000° C., for a time period of 1 minute to 30 minutes. Heating can, in particular, take place in an oven and/or by infrared irradiation. In general, an object temperature is selected to be slightly above the decomposition temperature in question. In general, heating, more precisely maintaining the object temperature, does not take longer than 15 minutes.

In particular when working with the embodiment of compositions according to the invention based on iridium complexes of type $[LIr[O(CO)R1]]_m$, it is advantageous that no colloidal iridium- or nanoiridium-containing compositions have to be used, so that any associated risks can be avoided.

In the second and third of the aforementioned application methods, clogging of the application tools, more precisely, clogging of fine openings or nozzles of spray application tools or inkjet nozzles is avoided through the use of the compositions according to the invention; and finally, for example, the question of colloidal iridium or nanoiridium drying or aggregating does not arise here.

The thickness of layers comprising iridium obtainable according to the invention can, for example, be in the range of 50 nm to 5 µm, preferably 200 nm to 2 µm, more preferably 300 nm to 1 µm, and the layers comprising iridium can have a planar nature with or without desired discontinuities within the surface area, or can have a desired pattern or design. As is apparent from the aforementioned examples of substrates, the layers comprising iridium can even be generated on temperature-sensitive substrates, i.e., for example, on substrates that are not temperature-stable above 200° C.; for example, they can be temperature-sensitive polymer substrates, for example those based on polyolefins or polyesters.

Electrodes can be applied onto a substrate, or existing electrodes can be coated, with the aid of the methods described herein.

In one embodiment, a second electrode is applied to or coated onto the substrate. In one embodiment, a second electrode is applied to or coated onto the substrate by inkjet printing.

In one embodiment, a second electrode is applied to or coated onto the substrate by inkjet printing of the composition described herein. In one embodiment, one electrode is configured as a working electrode, and the second electrode is configured as a reference electrode. In one embodiment, two electrodes are applied to or coated onto the substrate, and the two electrodes are configured to jointly detect an electrochemical potential.

A further aspect of the invention provides a medical electrode that is produced or can be produced according to a method described herein. Such an electrode can in particular have the advantageous properties described herein of improved impedance, charge storage, and/or a smooth surface topography of the iridium oxide layer. The medical electrode can be configured for implantation, for example into the human body. In one embodiment, the medical electrode is configured for direct tissue contact. In one embodiment, the medical electrode is biocompatible. The electrode can be configured to deliver an electrical signal to the human body. The electrode can be configured to receive an electrical signal from the human body.

The electrode comprises a substrate which is used as a base body and to support the iridium layer. The electrode can comprise a flexible substrate made of plastic, for example. The substrate can, for example, be a polymer film, for example a film made of PTFE or polyimide. The substrate can also be a wire, for example a metal wire. The iridium layer can be structured and contain, for example, one or more contact elements, one or more conductor tracks, and an electrical element configured to receive and/or output an electrical signal. The electrode can furthermore comprise an encapsulation. The encapsulation can be composed of a biocompatible material, for example platinum, titanium, or a medical silicone. The encapsulation can include a feed-through so that the active part of the electrode can be led out of the encapsulation. In one embodiment, only the active part of the design protrudes from the encapsulation. The active part can comprise part of the substrate and of the iridium oxide layer situated thereon.

In one embodiment, the electrode is produced or can be produced by an inkjet method. In one embodiment, the iridium layer of the electrode is produced or can produced by applying the composition according to the invention onto a substrate by means of an inkjet method. In one embodiment, the electrode is produced or can be produced by printing, dip coating, spray coating, spin coating, or knife coating the composition according to the invention onto a substrate.

A further aspect of the invention relates to a medical electrode comprising a printed iridium oxide layer.

A further aspect of the invention relates to a medical electrode that comprises a flexible carrier substrate coated with an iridium oxide layer.

The flexible carrier substrate can, for example, comprise a film comprising one of the plastic materials described herein or consisting thereof. The carrier substrate can preferably be a so-called flex PCB, i.e., a film-based printed circuit board. Such substrates can, for example, comprise liquid crystal polymers (LCPs), as described herein. In particular, the conductor tracks on the flex PCB can be coated with a smooth iridium oxide layer by means of the methods described herein.

In one embodiment, an electrode according to the invention shows, in a cyclic voltammetry measurement under the measurement conditions in Example 6, a charge storage capacity CSC of at least 30, 40, or at least 50 mC/cm$^2$.

A further aspect of the invention relates to the use of a method as described herein for producing a medical electrode.

A further aspect of the invention relates to a solution of an organic iridium complex compound in a solvent, whose solubility in propylene glycol monopropyl ether at 25° C. and 1013 hPa is at least 1, preferably at least 2, 3, 4, 5, or 10% by mass.

The solvent can be any solvent described herein. In one embodiment, the solvent is a non-aqueous solvent. In one embodiment, the ET30 value of the solvent is 30 to 52 kcal/mol, 30 to 50 kcal/mol, or 35 to 45 kcal/mol. In one embodiment, the ET30 value of the solvent is 120 to 240 kJ/mol, 125 to 220 kJ/mol, or 160 to 200 kJ/mol. When the solvent is a solvent mixture, the ET30 value refers to the solvent mixture.

In one embodiment, the solvent is suitable for inkjet printing, preferably for inkjet printing on plastic or metal surfaces.

In one embodiment, the solution comprises
(a) a non-aqueous solvent (also referred to herein as component (A)), and
(b) an organic iridium complex compound (also referred to herein as component (B)) dissolved in the solvent, as described herein for the other aspects.

Optionally, the solution can furthermore contain 0 to 10% by weight, preferably 0 to 3% by weight, of at least one additive. Accordingly, the solution can be additive-free or contain up to 10% by weight of at least one additive. Examples of additives include wetting additives, rheological additives, defoamers, deaerators, additives for influencing the surface tension, and odorants.

In one embodiment, the iridium complex compound is readily soluble in both polar and non-polar solvents.

In one embodiment, the solubility of the organic iridium complex compound in ethanol at 25° C. and 1013 hPa is at least 1, preferably at least 2, 3, 4, 5, or at least 10% by mass.

In one embodiment, the solubility of the organic iridium complex compound in toluene at 25° C. and 1013 hPa is at least 1, preferably at least 2, 3, 4, 5, or at least 10% by mass.

In one embodiment, the solubility of the organic iridium complex compound in a solvent mixture comprising eight parts of ethanol and two parts of water at 25° C. and 1013 hPa is at least 1, preferably at least 2, 3, 4, 5, or at least 10% by mass.

In one embodiment, the solubility of the organic iridium complex compound in ethanol is at least 1% by mass and in n-hexane is at least 1% by mass.

In one embodiment, the solubility of the organic iridium complex compound in ethanol is at least 1% by mass and in n-hexane is at least 1% by mass.

In one embodiment, the solubility of the organic iridium complex compound in ethanol is at least 2% by mass and in n-hexane is at least 2% by mass.

In one embodiment, the solubility of the organic iridium complex compound in ethanol is at least 3% by mass and in n-hexane is at least 3% by mass.

In one embodiment, the solubility of the organic iridium complex compound in ethanol is at least 4% by mass and in n-hexane is at least 4% by mass.

In one embodiment, the solubility of the organic iridium complex compound in ethanol is at least 5% by mass and in n-hexane is at least 5% by mass.

In one embodiment, the solubility of the organic iridium complex compound in ethanol is at least 10% by mass and in n-hexane is at least 10% by mass.

In one embodiment, the solubility of the organic iridium complex compound in ethanol is at least 2% by mass and in n-hexane is at least 1% by mass.

In one embodiment, the solubility of the organic iridium complex compound in ethanol is at least 2% by mass and in n-hexane is at least 3% by mass.

In one embodiment, the solubility of the organic iridium complex compound in ethanol is at least 2% by mass and in n-hexane is at least 4% by mass.

In one embodiment, the solubility of the organic iridium complex compound in ethanol is at least 2% by mass and in n-hexane is at least 5% by mass.

In one embodiment, the solubility of the organic iridium complex compound in ethanol is at least 2% by mass and in n-hexane is at least 10% by mass.

In one embodiment, the solubility of the organic iridium complex compound in propylene glycol monopropyl ether is at least 1% by mass, in ethanol is at least 1% by mass, and in n-hexane is at least 1% by mass.

In one embodiment, the solubility of the organic iridium complex compound in propylene glycol monopropyl ether is at least 1% by mass, in ethanol is at least 2% by mass, and in n-hexane is at least 2% by mass.

In one embodiment, the solubility of the organic iridium complex compound in propylene glycol monopropyl ether is at least 1% by mass, in ethanol is at least 3% by mass, and in n-hexane is at least 3% by mass.

In one embodiment, the solubility of the organic iridium complex compound in propylene glycol monopropyl ether is at least 1% by mass, in ethanol is at least 4% by mass, and in n-hexane is at least 4% by mass.

In one embodiment, the solubility of the organic iridium complex compound in propylene glycol monopropyl ether is at least 1% by mass, in ethanol is at least 5% by mass, and in n-hexane is at least 5% by mass.

In one embodiment, the solubility of the organic iridium complex compound in propylene glycol monopropyl ether is at least 1% by mass, in ethanol is at least 10% by mass, and in n-hexane is at least 10% by mass.

In one embodiment, the solubility of the organic iridium complex compound in propylene glycol monopropyl ether is at least 1% by mass, in ethanol is at least 2% by mass, and in n-hexane is at least 1% by mass.

In one embodiment, the solubility of the organic iridium complex compound in propylene glycol monopropyl ether is at least 1% by mass, in ethanol is at least 2% by mass, and in n-hexane is at least 3% by mass.

In one embodiment, the solubility of the organic iridium complex compound in propylene glycol monopropyl ether is at least 1% by mass, in ethanol is at least 2% by mass, and in n-hexane is at least 4% by mass.

In one embodiment, the solubility of the organic iridium complex compound in propylene glycol monopropyl ether is at least 1% by mass, in ethanol is at least 2% by mass, and in n-hexane is at least 5% by mass.

In one embodiment, the solubility of the organic iridium complex compound in propylene glycol monopropyl ether is at least 1% by mass, in ethanol is at least 2% by mass, and in n-hexane is at least 10% by mass.

In some embodiments, the organic iridium complex compound is virtually indefinitely soluble in the solvent. This means that the iridium complex compound and the solvent are miscible with each other in any proportion.

In one embodiment, the organic iridium complex compound is miscible in any proportion with a solvent selected from the group consisting of 1,5-cyclooctadiene (also referred to herein as COD), neodecanoic acid, norbornadiene, and cyclohexanoic acid.

A further aspect relates to the use of a composition described herein for producing a layer comprising iridium.

A further aspect relates to the use of a composition described herein for producing a medical electrode.

A further aspect of the invention relates to a composition comprising the following components:
(a) a non-aqueous solvent (also referred to herein as component (A)), and
(b) an organic iridium complex compound (also referred to herein as component (B)) dissolved in the solvent.

In one embodiment, the solubility of the organic iridium complex compound in propylene glycol monopropyl ether at 25° C. and 1013 hPa is at least 1, preferably at least 2, 3, 4, 5, or 10% by mass.

In one embodiment, the solubility of the organic iridium complex compound in ethanol at 25° C. and 1013 hPa is at least 1, preferably at least 2, 3, 4, 5, or 10% by mass.

In one embodiment, the solubility of the organic iridium complex compound in toluene at 25° C. and 1013 hPa is at least 1, preferably at least 2, 3, 4, 5, or 10% by mass.

In one embodiment, the solubility of the organic iridium complex compound in a solvent mixture comprising eight parts of ethanol and two parts of water at 25° C. and 1013 hPa is at least 1, preferably at least 2, 3, 4, 5, or 10% by mass.

In one embodiment, the organic iridium complex compound is measurable in any proportion with a solvent selected from the group consisting of glycol ether, 1,5-cyclooctadiene (also referred to herein as COD), neodecanoic acid, norbornadiene, and cyclohexanoic acid.

EXAMPLES

The invention is furthermore illustrated below based on specific examples which, however, are not to be understood as restrictive.

Example 1: Coating a Polyimide Film with an Iridium Oxide Layer

A solution of 16.3 mmol $[(COD)IrCl]_2$ in 200 ml dichloromethane was stirred, and a solution of 65.3 mmol sodium neodecanoate in 100 ml water was added. The two-phase mixture was emulsified for 24 h at 20° C. by vigorous stirring. The dichloromethane phase turned yellow in the process.

The dichloromethane phase was separated, and the solvent was distilled off. The viscous, yellow residue was placed in petroleum benzine (40-60), and the solution was dried with magnesium sulfate and filtered. Next the petroleum benzine was completely distilled off. A viscous yellow residue of $[(COD)Ir[O(CO)(CH_2)_5C(CH_3)_3]]_m$ remained.

5 g of the yellow residue was dissolved in 5 g of petroleum benzine. This solution was sprayed onto a Kapton® film by means of an airbrush spray gun. The coated film was heated in a laboratory oven to an object temperature of 250° C. and kept at this temperature for 3 minutes. A matte layer made substantially of iridium oxide had formed on the film.

Example 2: Coating a Polyimide Film with a Patterned Iridium Oxide Layer

A Kapton® film was printed with the solution from Example 1 with the aid of an inkjet printer at a resolution of 1270 dpi in a meander design. The film thus printed was heated in a laboratory oven to an object temperature of 250° C. and kept at this temperature for 5 minutes. A matte layer consisting substantially of iridium oxide in the shape of the meander design, having a width of the conductor tracks of 2.5 mm, had formed on the film.

Example 3: PVD Coating of a PtIr Strip with an Iridium Oxide Layer (Comparative Example)

An iridium oxide layer having a layer thickness of approximately 0.4 µm was applied to a PtIr10 strip having a thickness of 100 µm and a surface area of 25 mm×6 mm by means of a reactive DC magnetron sputtering process. For this purpose, an Ir target (99.9% purity) and oxygen were used as reactive gas.

Example 4: Coating of a PtIr Strip with an Iridium Oxide Layer by Knife Coating

A PtIr10 strip having a thickness of 100 µm and a surface area of 25 mm×6 mm was coated by knife coating with the compound produced in Example 1 $[(COD)Ir[O(CO)(CH_2)_5C(CH_3)_3]]_m$, dissolved in $CH_2Cl_2$ (10%). For this purpose, a drop of the liquid composition was placed on the strip, and the liquid was evenly distributed on the surface. The samples were heated for 5 min at 200-250° C. at normal pressure and in ordinary ambient air, which resulted in the decomposition of the compound, thereby forming an iridium oxide layer on the PtIr strip. Some samples were then coated again as described above and heated to apply a second iridium oxide layer. Scanning electron microscope images (see FIG. 1) showed that the iridium oxide layer formed surprisingly had a very smooth surface topography. In particular, no rough and jagged "cauliflower structures" known from the prior art were observed, for example as shown in US20140326482A1 (see in particular FIGS. 4 and 4A). The layer thickness of the iridium oxide layer (with a single coating) was approximately 1 to 2 µm according to the SEM measurement. With the aid of XPS and AES measurements, it was confirmed that the material of the coating was iridium oxide.

Example 5: EIS Measurements

The samples produced in Examples 3 and 4 were subjected to electrochemical impedance spectroscopy (EIS)

(frequency range 100 kHz to 0.1 Hz, excitation amplitude 10 mV, PBS buffer (phosphate-buffered saline; 8 g/L NaCl, 0.2 g/L KCl; 1.15 g/L Na$_2$HPO$_4$, and 0.2 g/L KH$_2$PO$_4$; pH 7.4), measurement taking place under inert conditions). The measured values obtained for the impedance Z and the limit frequency f$_G$ after 60 cyclic voltammetry cycles are shown in Table 2. The samples according to the invention from Example 4 show significantly lower impedance values than the sample from the comparative Example 3. The comparison of the samples coated once and twice by means of the composition according to the invention shows that the layer thickness has a smaller influence on the impedance than the coating method used. Accordingly, the coating according to the invention according to Example 4 results in improved impedance properties of the iridium oxide layer.

TABLE 2

Measurement results of the EIS measurements according to Example 5

| Sample | Z/Ω | | f$_G$/Hz |
|---|---|---|---|
| | 1 Hz | 10 Hz | |
| Reference PtIr10 | 155945 | 27085 | 1000 |
| Sample from Example 3, PVD coating | 1577 | 465 | 4 |
| Sample from Example 4, coated once | 676 | 358 | 2 |
| Sample from Example 4, coated twice | 729 | 398 | 2 |

Example 6: Cyclic Voltammetry Measurements

The samples produced in Examples 3 and 4 were subjected to cyclic voltammetry measurements (reverse potential: −650 mV to 750 mV, sampling rate 100 mV/s, PBS buffer (see Example 5), inert conditions). The measured values obtained after 60 cyclic voltammetry cycles are shown in Table 3. The samples according to the invention from Example 4 show significantly higher values in the measured charge storage capacity (CSC) than does the sample from the comparative Example 3. The comparison of the samples coated once and twice by means of the composition according to the invention shows that the layer thickness has a smaller influence on the charge storage capacity than does the coating method used. Accordingly, the coating according to the invention according to Example 4 results in improved impedance properties of the iridium oxide layer.

TABLE 3

Measurement results of the cyclic voltammetry measurements according to Example 6

| Sample | CSC/[mC/cm$^2$] |
|---|---|
| Reference PtIr10 | 1.0 |
| Sample from Example 3, PVD coating | 24.0 |
| Sample from Example 4, coated once | 63.2 |
| Sample from Example 4, coated twice | 63.0 |

Example 7: Adhesive Tape Test

As in Example 4, PtIr strips were coated with the compound produced in Example 1 [(COD)Ir[O(CO)(CH$_2$)$_5$C(CH$_3$)$_3$]]$_m$, dissolved in ethanol:propylene glycol (1:1), by knife coating and heated for 10 minutes in an ordinary ambient atmosphere to 250° C., wherein an iridium oxide layer formed. Some of the PtIr strips were roughened by shot blasting (grit blasting) prior to coating. The coated strips were covered with strips of adhesive tape, and the adhesive tape strips were subsequently removed. No delamination of the iridium oxide layer was observed in any of the samples.

Example 8: Production of an Iridium Oxide Layer by Inkjet Printing

The composition from Example 7 was printed with the aid of an inkjet printer at a resolution of 1060 dpi or 1270 dpi onto a 100 μm-thick PtIr strip. The samples were then heated to 250° C. for 10 minutes in an ordinary ambient atmosphere, whereby an iridium oxide layer formed.

The invention claimed is:

1. A method for producing a medical electrode coated with iridium oxide, comprising the following steps:
   (i) providing a medical electrode having an electrode surface;
   (ii) applying a liquid composition to the electrode surface, the composition comprising an organic iridium complex compound;
   (iii) heating the composition in an oxygen-containing atmosphere, thereby forming an iridium oxide layer on the electrode surface, and
   wherein the liquid composition comprises an iridium complex comprising diolefin and C6-C18 monocarboxylate ligands of type [LIr[O(CO)R1]]$_m$, where L denotes a compound acting as a diolefin ligand, where —O(CO)R1 denotes a non-aromatic C6-C18 monocarboxylic acid radical, and where m is an integer ≥2.

2. The method according to claim 1, wherein the solubility of the organic iridium complex compound in propylene glycol monopropyl ether at 25° C. and 1013 hPa is at least 1% by mass, based on the total mass of the composition.

3. The method according to claim 2, wherein the solubility of the organic iridium complex compound in propylene glycol monopropyl ether at 25° C. and 1013 hPa is at least 10% by mass, based on the total mass of the composition.

4. The method according to claim 1, wherein the liquid composition comprises a non-aqueous solvent.

5. The method according to claim 1, wherein step (iii) is carried out above a decomposition temperature of the iridium complex compound but below a lowest melting or decomposition temperature of a material of the electrode surface.

6. The method according to claim 1, wherein the electrode surface comprises a metal, a ceramic, or a plastic, or consists at least in sections of metal, ceramic, or plastic.

7. The method according to claim 1, wherein the liquid composition is applied using a method selected from the group consisting of printing, dip coating, spray coating, spin coating, knife coating, and application by means of a saturated application tool.

8. The method according to claim 1, wherein the heating, and thereby the formation of an iridium oxide layer, is carried out at a temperature of less than 1000° C.

9. The method according to claim 8, wherein the heating, and thereby the formation of an iridium oxide layer, is carried out at a temperature of less than 150° C.

10. The method according to claim 1, wherein the heating, and thereby the formation of an iridium oxide layer, is carried out at a pressure of between 750 and 1250 hPa.

11. The method according to claim 1, wherein the application of the composition to the electrode surface takes place selectively in a shape of a predetermined pattern so that the formed iridium oxide layer is given the shape of the predetermined pattern.

12. The method according to claim 1, wherein steps (ii) and (iii) are repeated once or several times in order to incrementally build up a thicker iridium oxide layer.

13. The method according to claim 1, wherein L is cyclooctadiene or norbornadiene, n is 1 or 2, m is 2, and R1 is a non-aromatic C5-C17 hydrocarbon radical.

14. The method according to claim 1, wherein the iridium oxide layer has a thickness of from 50 nm to 5 μm.

15. The method according to claim 14, wherein the iridium oxide layer has a thickness of from 300 nm to 1 μm.

\* \* \* \* \*